US009079952B2

(12) United States Patent
Collier et al.

(10) Patent No.: US 9,079,952 B2
(45) Date of Patent: Jul. 14, 2015

(54) METHOD FOR DELIVERING AGENTS INTO CELLS USING BACTERIAL TOXINS

(75) Inventors: Robert J. Collier, Wellesley, MA (US); Brad L. Pentelute, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/978,550

(22) PCT Filed: Jan. 10, 2012

(86) PCT No.: PCT/US2012/020731
§ 371 (c)(1),
(2), (4) Date: Sep. 3, 2013

(87) PCT Pub. No.: WO2012/096926
PCT Pub. Date: Jul. 19, 2012

(65) Prior Publication Data

US 2013/0336974 A1 Dec. 19, 2013

Related U.S. Application Data

(60) Provisional application No. 61/431,272, filed on Jan. 10, 2011.

(51) Int. Cl.

| | |
|---|---|
| ***C07K 11/00*** | (2006.01) |
| ***C12P 21/08*** | (2006.01) |
| ***C07K 14/195*** | (2006.01) |
| ***C07K 16/46*** | (2006.01) |
| ***C12N 9/52*** | (2006.01) |
| *A61K 38/00* | (2006.01) |

(52) U.S. Cl.
CPC ............... *C07K 14/195* (2013.01); *C07K 16/46* (2013.01); *C12N 9/52* (2013.01); *A61K 38/00* (2013.01); *C07K 2319/10* (2013.01); *C07K 2319/50* (2013.01); *C07K 2319/55* (2013.01)

(58) Field of Classification Search
None
See application file for complete search history.

(56) References Cited

U.S. PATENT DOCUMENTS

| | | | | |
|---|---|---|---|---|
| 6,287,556 | B1 | 9/2001 | Portnoy et al. | |
| 6,592,872 | B1 | 7/2003 | Klimpel et al. | |
| 6,846,484 | B2 | 1/2005 | Vallera et al. | |
| 6,916,917 | B1 * | 7/2005 | Baltimore et al. | 536/23.4 |
| 2003/0124147 | A1 | 7/2003 | Vallera et al. | |
| 2003/0202989 | A1 * | 10/2003 | Collier et al. | 424/236.1 |
| 2009/0142794 | A1 | 6/2009 | Leppla et al. | |
| 2010/0215575 | A1 | 8/2010 | O'Neill et al. | |
| 2010/0311105 | A1 | 12/2010 | Lu et al. | |

FOREIGN PATENT DOCUMENTS

| | | | | |
|---|---|---|---|---|
| WO | 94/18332 | A2 | 8/1994 | |
| WO | WO0050872 | A2 * | 8/2000 | G01N 15/14 |
| WO | 2011/133704 | A2 | 10/2011 | |

OTHER PUBLICATIONS

Abrami et al., The Journal of Cell Biology, 166(5):645-651 (2004). "Membrane insertion of anthrax protective antigen and cytoplasmic delivery of lethal factor occur at different stages of the endocytic pathway."
Basilio et al., J. Gen. Physiol., 133(3):307-314 (2009). "Evidence for a Proton-Protein Symport Mechanism in the Anthrax Toxin Channel."
Bradley et al., Nature, 414:225-229 (2001). "Identification of the cellular receptor for anthrax toxin."
Dawson et al., Science, 266:776-778 (1994). "Synthesis of Proteins by Native Chemical Ligation."
Duesbery et al., Science, 280:734-737 (1998). "Proteolytic Inactivation of MAP-Kinase-Kinase by Anthrax Lethal Factor."
Finkelstein, Phil. Trans. R. Soc. B, 364:209-215 (2009). "Proton-coupled protein transport through the anthrax toxin channel."
Katayama et al., Nature Structural and Molecular Biology, 15(7):754-760 (2008). "GroEL as a molecular scaffold for structural analysis of the anthrax toxin pore."
Kintzer et al., J. Mol. Biol., 392:614-629 (2009). "The Protective Antigen Component of Anthrax Toxin Forms Functional Octameric Complexes."
Klimpel et al., Proc. Natl. Acad. Sci., 89:10277-10281 (1992). "Anthrax toxin protective antigen is activated by a cell surface protease with the sequence specificity and catalytic properties of furin."
Krantz et al., Science, 309:777-781 (2005). "A Phenylalanine Clamp Catalyzes Protein Translocation Through the Anthrax Toxin Pore."
Krantz et al., J. Mol. Biol., 355:968-979 (2006). "Protein Translocation through the Anthrax Toxin Transmembrane Pore is Driven by a Proton Gradient."
Leppla, Proc. Natl. Acad. Sci., 79:3162-3166 (1982). "Anthrax toxin edema factor: A bacterial adenylate cyclase that increases cyclic AMP concentrations in eukaryotic cells."
McCluskey et al., Molecular Oncology, 7:440-451 (2013). "Targeting HER2-positive cancer cells with receptor-redirected anthrax protective antigen."
Mechaly et al., mBio, 3(3):e00088-12 (2012). "Changing the Receptor Specificity of Anthrax Toxin."
Milne et al., The Journal of Biological Chemistry, 269(32):20607-20612 (1994). "Anthrax Protective Antigen Forms Oligomers during Intoxication of Mammalian Cells."

(Continued)

*Primary Examiner* — Gary Nickol
*Assistant Examiner* — Khatol Shahnan Shah
(74) *Attorney, Agent, or Firm* — Nixon Peabody LLP; David S. Resnick; Leena H. Karttunen Contarino

(57) ABSTRACT

The invention provides compositions and methods for delivering a bioactive moiety comprising at least one non-natural component into a cell cytosol of an eukaryotic cell. The bioactive moiety is linked to an A component of a bacterial toxin, a functional wild-type or modified fragment thereof, or an A component surrogate or mimetic. For delivery, the cell is contacted with the linked bioactive moiety and a corresponding B component of the bacterial toxin or a functional fragment thereof.

39 Claims, 9 Drawing Sheets

(56) References Cited

OTHER PUBLICATIONS

Molloy et al., The Journal of Biological Chemistry, 267(23):16369-16402 (1992). "Human Furin is a Calcium-dependent Serine Endoprotease That Recognizes the Sequence Arg-X-X-Arg and Efficiently Cleaves Anthrax Toxin Protective Antigen."

Pentelute et al., ACS Chemical Biology, 5(4):359-364 (2010). "A Semisynthesis Platform for Investigating Structure—Function Relationship in the N-Terminal Domain of the Anthrax Lethal Factor."

Rogers et al., Cancer Res, 67:9980-9985 (2007). "Mutant Anthrax Toxin B Moiety (Protective Antigen) Inhibits Angiogenesis and Tumor Growth."

Schnolzer et al., Int. J. Peptide Protein Res., 40:180-193 (1992). "In situ neutralization in Box-chemistry solid phase peptide synthesis."

Scobie et al., PNAS, 100(9):5170-5174 (2003). "Human capillary morphogenesis protein 2 functions as an anthrax toxin receptor."

Sellman et al., The Journal of Biological Chemistry, 276(11):8371-8376 (2001). "Point Mutations in Anthrax Protective Antigen That Block Translocation."

Vitale et al., Biochemical and Biophysical Research Communications, 248:706-711 (1998). "Anthrax Lethal Factor Cleaves the N-Terminus of MAPKKs and Induces Tyrosine/Threonine Phosphorylation of MAPKs in Cultured Macrophages."

Williams et al., Protein Engineering, 1(6):493-498 (1987). "Diphtheria toxin receptor binding domain substitution with interleukin-2: genetic construction and properties of a diphtheria toxin-related interleukin-2 fusion protein."

Young et al., Annu. Rev. Biochem., 76:243-265 (2007). "Anthrax Toxin: Receptor Binding, Internalization, Pore Formation, and Translocation."

Zhang et al., PNAS, 101(48):16756-16761 (2004). "Evidence that translocation of anthrax toxin's lethal factor is initiated by entry of its N terminus into the protective antigen channel."

Rabideau et al., The Royal Society of Chemisty, DOI: 10.1039/c4sc02078b. "Delivery of mirror image polypeptides into cells." (First published online on Sep. 25, 2014).

Liao et al., Chem. Bio. Chem., DOI: 10.1002/cbic.201402290. "Delivery of antibody mimics into mammalian cells via anthrax toxin protective antigen." (First published online on Sep. 22, 2014).

Antos et al., J Am Chem Soc. 130(48):16338-16343. (2008). "Lipid modification of proteins through sortasecatalyzed transpeptidation."

Antos et al., J Am Chem Soc. 131(31):10800-10801 (2009). "Site-specific N- and C-terminal labeling of a single polypeptide using sortases of different specificity."

Arteaga et al., Nature, 9:16-32 (2012). "Treatment of HER2-positive breast cancer: current status and future perspectives."

Berchuck et al., Cancer Res. 50:4087-4091 (1990). "Overexpression of HER-2/neu is associated with poor survival in advanced epithelial ovarian cancer."

Cao et la., Cancer Res. 69:8987-8995 (2009). "Construction and characterization of novel, recombinant immunotoxins targeting the Hers/neu oncogene product: in vitro and in vivo studies."

Cao et al., Mol Cancer Ther. 12:979-991 (2013). "Construction and characterization of novel, completely human serine protease therapeutics targeting her/neu."

Carter et al., Proc. Natl. Acad. Sci. 89:4285-4289 (1992). "Humanization of an anti-p185 HER2 antibody for human cancer therapy."

Chen et al., PNAS 108(28):11399-11404 (2011). "A general strategy for the evolution of bond forming enzymes using yeast display."

Collier et al., Science 164:1179-1182 (1969). "Diphtheria Toxin Subunit active in vitro."

Collier et al., Mol Aspect Med. 30(6):413-422 (2009). "Membrane translocation by anthrax toxin."

Collier et al., J. Mol. Biol. 25:83-98 (1967). "Effect of Diphtheria toxin on protein synthesis: Inactivation of one of the transfer factors."

Cunningham et al., PNAS, 99(10):7049-7053 (2002). "Mapping the lethan factor and edema factor binding sites on oligomeric anthrax protective antigen."

Gravalos et al., Annls of Oncology 19:1523-1529 (2008). "HER2 in gastric cancer: a new prgnostic factor and a novel therapeutic target."

Guimaraes et al., J. Cell Biol. 195(5):751-764 (2011). "Identification of host cell factors required for intoxication through use of modified cholera toxin."

Ilangovan et al., PNAS, 98(11):6056-6061 (2001). "Structure of sortase, the transpeptidase that anchors protein to the cell wall of *Staphylococcus aureus*."

Kobashigawa et al. J. Biomol. NMR 43:145-150 (2009). "Attachment of an NMR-invisible solubility enhancement tag using a sortase-mediated protein ligation method."

Kruger et al., Biochemistry, 43:1541-1551 (2004). "Analysis of the substrate specificity of the *Staphylococcus aureus* sortase transpeptidase SrtA."

Levary et al., PLOS ONE 6(4):e18342 (2011). "Protein-Protein fusion catalyzed by sortase A".

Ling et al., J Am Chem Soc., 134(26):10749-10752 (2012). "Protein thioester synthesis enabled by sortase."

Mao et al., J. Am Chem Soc. 126:2670-2671 (2004). "Sortase-mediated protein ligation: a new method for protein engineering."

Mogridge et al., PNAS 99(10):7045-7048 (2002). "The lethal and edema factors of anthrax toxin bind only to oligomeric forms of the protective antigen."

Orlova et al., Cancer Res. 66:4339-4348 (2006). "Tumor Imaging Using a picomolar affinity HER2 binding afhbody molecule."

Popp et al., Nature Chemical Biology 11(3):707-708 (2007). "Sortagging: a versatile method for protein labeling."

Pritz et al., J. Org. Chem. 72:3909-3912 (2007). "Synthesis of Biologically active peptide nucleic acid-peptide conjugates by sortase-mediated ligation."

Rosovitz et al., J. Biol. Chem. 278:30936-30944 (2003). "Alanine-scanning mutations in Domain 4 of Anthrax toxin protective antigen reveal residues important for binding to the cellular receptor and to a neutralizing monoclonal antibody."

Samantaray et al., J. Am. Chem. Soc. 130:2132-2133 (2008). "Peptide-sugar ligation catalyzed by transpeptidase sortase: A facile approach to neoglycoconjugate synthesis."

Slamon et al., Science 244:707-712 (1989). "Studies of the HER-2/neu Proto-oncogene in human breast and ovarian cancer."

Ton-That et al., PNAS 96(22):12424-12429 (1999). "Purification and characterization of sortase, the transpeptidase that cleaves surface proteins of *Staphylococcus aureus* at the LPXTG motif."

Venkataraman et al. PLOS Biology 7(4):e1000095 (2009). "Reawakening retrocyclins: ancestral human defensins active against HIV-1."

Wesche et al., Biochemistry 37:15737-15746 (1998). "Characterization of membrane translocation by anthrax protective antigen."

Zielinski et al., Clin Cancer Res. 17:5071-5081 (2011). "HER2-Affitoxin: A potent therapeutic agent for the treatment of HER2-overexpression tumors."

Pentelute et al., ACS Chemical Biology 5(4):359-364 (2010). "A semisynthesis platform for investigating structure-function relationships in the N-Terminal domain of the anthrax lethal factor."

Pentelute et al., Angew. Chem. Int. Ed. 50:2294-2296 (2011). "Chemical dissection of protein translocation though the anthrax toxin pore."

Leppla et al. Journal of Applied Microbiology, 87:284 (1999). "Anthrax toxin fusion proteins for intracellular delivery of macromolecules."

Bunt et al., Optical Fluorescence Microscopy, Springer-Verlag Berlin Heidelberg, 111-130 (2011). "Chapter 7: Site-Specific Labeling of Proteins in Living Cells using synthetic fluorescent dyes."

Sakamoto et al., Bioconjugate Chem., 21:2227-2233 (2010). "Enzyme-Mediated Site-Specific Antibody Protein modification using a ZZ domain as a linker."

Shapira et al., Toxins, 2:2519-2583 (2010). "Toxin-based therapuetic approaches".

Wu et al., Journal of Carbohydrate Chemistry, 31(1):48-66 (Epub. 2012). "Sortase-mediated transpeptidation for site-specific modification of peptides, glycopeptides and proteins."

* cited by examiner

D-AMINO ACID

N-METHYL

HOMO AMINO ACIDS

CYLIC PEPTIDES

METHOD FOR DELIVERING AGENTS INTO CELLS USING BACTERIAL TOXINS

CROSS-REFERENCE TO RELATED APPLICATIONS

This application is a 35 U.S.C. §371 National Phase Entry Application of International Application No. PCT/US2012/020731 filed Jan. 10, 2012, which designates the U.S., and which claims benefit under 35 U.S.C. §119(e) of U.S. Provisional Patent Application No. 61/431,272 filed on Jan. 10, 2011,the contents of which are herein incorporated by reference in their entirety.

GOVERNMENT SUPPORT

This invention was made with government support under grant number RO1 AI022021 awarded by National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 28, 2013, is named 002806-069302 SL.txt and is 21,567 bytes in size.

FIELD OF THE INVENTION

In general, the invention relates to methods for delivering molecules, particularly non-natural proteins, peptides and other chemical entities into cells.

BACKGROUND OF THE INVENTION

An important goal for researchers and pharmaceutical companies is to identify ways to use proteinaceous delivery vehicles to introduce novel molecules into the cytosol of cells, particularly into mammalian cells. While there are a number of methods for the delivery of bioactive peptides and proteins into mammalian cells for therapeutic and biotechnological purposes, there is still a specific need for methods to deliver larger molecules such as peptides, peptoids, proteins and small molecules that cannot traverse the plasma membrane by a simple diffusive process. Particularly, there is a need to deliver agents that are non-naturally occurring such modified peptides, D-peptides and other organic molecules not normally trafficked into a cell or manufactured by a cell.

The current technologies used to gain therapeutic access to the cytosol are limited in that they require large quantities of sample, have limited selectivity, and tend to not escape the endosome. The so called undruggable cytosolic fraction constitutes 80% of future therapeutic targets. Efficient delivery of the novel therapeutics is the main hurdle in drug development.

SUMMARY OF THE INVENTION

Here we provide a methodology that allows for the efficient delivery of bioactive peptide and protein molecules containing non-natural amino acids and/or other chemical entities into the cytosol of eukaryotic cells. This invention allows for the delivery of chemical entities including D-peptides/proteins, cyclic peptides/proteins, and variants containing a wide-range of non-natural amino acids and other chemical entities to the cytosol of cells. We have discovered that modified versions of bacterial toxins, such as anthrax lethal toxin or other intracellularly acting toxins, such as diphtheria toxin or cholera toxin, can be used in efficient delivery of larger chemical entities, such as D-peptides/proteins, cyclic peptides/proteins, and variants containing a wide-range of non-natural amino acids into cytosol.

We have also established semisynthetic platforms that rely on native chemical ligation and/or sortase tagging for the covalent attachment of the novel chemical entities to toxins. Bioactive chemical entities may be attached to generate a "pro-form", so that, once within the cytosol, the bioactive molecule can be released from the toxin by proteolytic cleavage.

This technology is not specific to anthrax lethal toxin in that also other bacterial toxins may be used as delivery vehicles. Such other toxins include, e.g., cholera toxin, diphtheria toxin, Pertussis toxin, *E. coli* heat-labile toxin LT, *Pseudomonas* Exotoxin A, *Bordetella pertussis* AC toxin, Botulinum toxin, Tetanus toxin, and Shiga toxin.

In addition, specific cell types may be targeted by modifying the receptor binding domain (B) of the respective toxin.

In one aspect, the invention provides a method for delivering a bioactive moiety comprising at least one non-natural component into a cell cytosol comprising contacting the cell with (a) a fusion molecule comprising the bioactive moiety attached to an A component of a bacterial toxin or a functional wild-type or modified fragment thereof or an A component surrogate or mimetic and (b) a corresponding B component of the bacterial toxin or a functional fragment thereof.

In some aspects, the A component of a bacterial toxin or a functional wild-type or modified fragment thereof is selected from sequences set forth in FIG. 2A (SSv1, Ssv2, Ssv3 and Ssv4).

In some aspects the B component is an anthrax protective antigen (PA).

In some aspects, the method further comprised a step of attaching the bioactive moiety to the A component of a bacterial toxin or the functional wild-type or modified fragment thereof to form the fusion molecule.

In some aspects, the fusion molecule further comprises a protease cleavage sequence between the bioactive moiety and the A component of a bacterial toxin or functional wild-type or modified fragment thereof.

In some aspects, the method further comprises a step of introducing a protease cleavage sequence into the fusion molecule to allow protease mediated release of the bioactive moiety from the A component after its entry into the cytosol.

In some aspects, the protease cleavage sequence is selected from a calpain, a caspase, and a cathepsin cleavage sites.

In some aspects, the protease cleavage sequence is selected from Caspase-8 (LETD (SEQ ID NO: 1)), Calpain (EPLFAERK (SEQ ID NO: 2)) and Calthepsin L (LWMRFA (SEQ ID NO: 3)).

In some aspects, the A and B components are selected from the family of intracellularly acting toxins. Exemplary intracellularly acting toxins include, but are not limited to, botulinum neurotoxin, anthrax toxin, diphtheria toxin, shiga toxin, shiga like toxin, exotoxin A, tetanus toxin, and cholera toxin.

Accordingly, in some aspects, the A and B components are selected from botulinum neurotoxin, diphtheria toxin, shiga toxin, shiga-like toxin, exotoxin A, tetanus toxin, and cholera toxin or functional fragments or variants thereof that are capable of transporting the bioactive moiety into the cell cytosol.

In some aspects, the bioactive moiety is attached to the C-terminus of the A component of the bacterial toxin or a functional wild-type or modified fragment thereof. In some embodiments, N-terminal attachment can be used.

In some aspects, A and B components are provided as separate molecules. In some aspect they are part of one single molecule.

In some aspects, the attaching is performed using native ligation or sortase mediated protein ligation.

In one aspect, the invention also provides a fusion molecule comprising a bioactive moiety comprising at least one non-natural component and an A component of a bacterial toxin or a functional variant or fragment thereof.

In some embodiments, the fusion molecule comprises an A component of bacterial toxin or a functional variant or fragment thereof selected from the sequences set forth in FIG. 2A (SSv1 (SEQ ID NO: 14), SSv2, SSv3 (SEQ ID NO: 15) and SSv4).

In some embodiments, the fusion molecule further comprises a protease cleavage sequence between the bioactive moiety and the A component of bacterial toxin or a functional variant or fragment thereof.

In some embodiments the bacterial toxin wherein the A and B parts are derived is selected from the group consisting of botulinum neurotoxin, anthrax toxin, diphtheria toxin, shiga toxin, shiga like toxin, exotoxin A, and cholera toxin.

In some embodiments, the protease cleavage sequence is selected from a calpain, a caspase, and a cathepsin cleavage sites.

In some embodiments, the protease cleavage sequence is selected from Caspase-8 (LETD (SEQ ID NO: 1)), Calpain (EPLFAERK (SEQ ID NO: 2)) and Calthepsin L (LWMRFA (SEQ ID NO: 3)).

In one aspect, the invention also provides a composition comprising the fusion molecule of any of the embodiments described herein. The composition may be a pharmaceutical composition comprising a pharmaceutically acceptable carrier.

In one aspect, the invention provides a kit comprising the fusion molecules or mixtures thereof as set forth above, the pharmaceutical composition comprising the same and a B component of the bacterial toxin.

In one embodiment, the B component is an anthrax protective antigen (PA).

In some aspects the bioactive molecule attached to the A-component or a functional fragment thereof is not, i.e. excludes, unmodified DNA molecules, unmodified RNA molecules, PNA molecules or unmodified proteins or peptides consisting only of L-amino acids.

BRIEF DESCRIPTION OF THE DRAWINGS

FIG. 1A shows the N-terminal 28 amino acid residues of LF (SEQ ID NO: 13), with the highly charged region underlined. FIG. 1B is an illustration of the N-terminal binding domain of Lethal Factor, LFN(1-263), indicated with a ribbon-structure, bound to PA pore. The pore structure was reconstructed from single-pore images obtained by electron microscopy (H. Katayama, B. E. Janowiak, M. Brzozowski, J. Juryck, S. Falke, E. P. Gogol, R. J. Collier, M. T. Fisher, Nat Struct Mol Bio12008, 15, 754) The black (basic), dotted (negative), and white (neutral) circles represent the unstructured N-terminal stretch of LF(12-28), which was not present in the X-ray structure of LF (PDB 1J7N). FIG. 1C shows a semisynthesis strategy used to prepare LFN constructs with modifications in the (12-28) amino acid stretch.

FIG. 2A shows a chemical framework of SSv1 (SEQ ID NO: 14), SSv2, SSv3 (SEQ ID NO: 15) and SSv4. FIG. 2B shows the fraction ion conductance block of PA pore by LFN variants at $\Delta\Psi$=20 mV ($\Delta\Psi$=cis−$\Psi$trans, where $\Psi$trans≡0). Each blocking experiment was repeated three times. FIG. 2C shows acid triggered translocation of LFN variants through PA pore in response to a pH gradient of ~2 units (cis pH 5.5; trans pH 7.5) at $\Delta\Psi$=20 mV. FIG. 2D shows translocation of LFN-DTA variants through PA pore in response to a pH gradient of ~2 units (cis pH 5.5; trans pH 7.5) at $\Delta\Psi$=20 mV. FIG. 2E shows fraction protein synthesis inhibition by LFN-DTA variants in CHO-K1 cells. LFN-DTA variants were incubated at the indicated concentration for 15-17 minutes at 37° C. and 5% CO2. Then, 3H-leucine was added, and after 1 hour the amount of tritium incorporated into cellular protein was measured. The data shown are the average of three experiments.

FIG. 3A shows chemical framework of SSv5 (SEQ ID NO: 16) and SSv6 (SEQ ID NO: 17)(X=cysteic acid). FIG. 3B shows the fraction ion conductance block of PA pore by SSv5 and SSv6 at $\Delta\Psi$=20 mV. FIG. 3C shows translocation of LFN variants through PA pore in response to a pH gradient of ~2 units (cis pH 5.5; trans pH 7.5) at $\Delta\Psi$=20 mV. FIG. 3D shows acid triggered translocation of LFN-DTA variants through PA pore in response to a pH gradient of ~2 units (cis pH 5.5; trans pH 7.5) at $\Delta\Psi$=20 mV. FIG. 3E shows fraction protein synthesis inhibition by LFN-DTA variants in CHO-K1 cells. The procedure used was identical to that described in FIG. 2E.

FIG. 4A shows cell entry and endosomal escape pathway for lethal toxin. FIG. 4B shows an X-ray structure of lethal factor with the N-terminal domain (LFN) in black. FIG. 4C shows a cartoon representation of LFN (indicated with a ribbon structure) interacting with PA pore.

FIG. 6A shows attachment by use of native chemical ligation. FIG. 6B shows attachment by use of the transpeptidase Sortase A. LPSTG (SEQ ID NO: 18).

DETAILED DESCRIPTION OF THE INVENTION

Figure 4A:
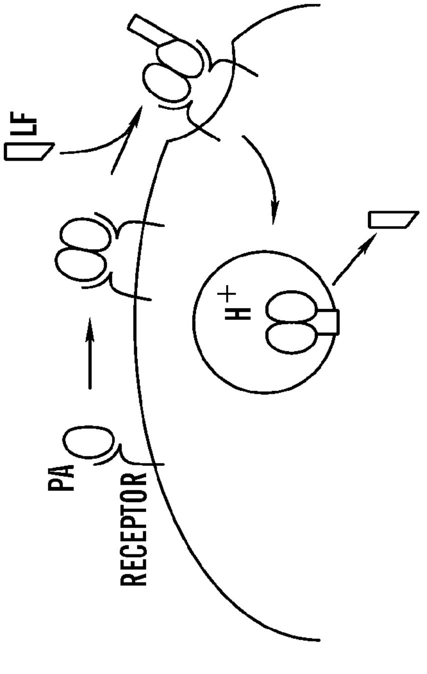
FIGS. 4A-4C show various aspects of anthrax lethal toxin.
Figure 4B:
Figure 4C:
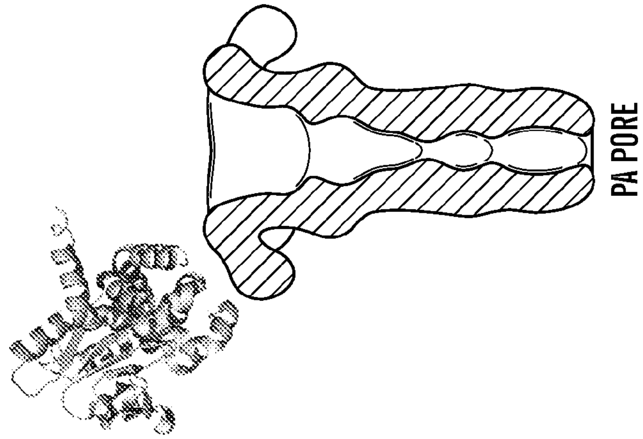
Figure 5:
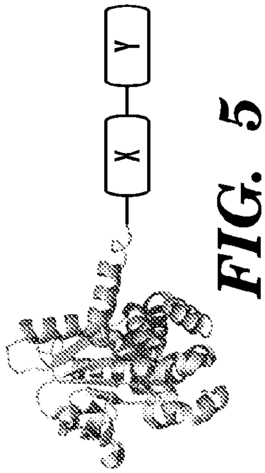
FIG. 5 shows modified form of LFN for the delivery of novel chemical entities into the cytosol of cells. X and Y are appended to the C-terminus of LFN. X is a specific protease cleavage site for release of Y which is the novel chemical entity.
Figure 6A:
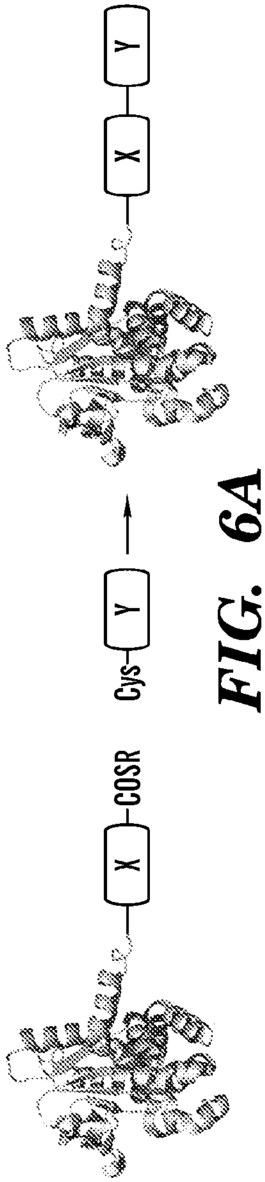
FIGS. 6A-6B show methodologies for the covalent attachment of chemical entities to the C-terminus of LFN.
Figure 6B:
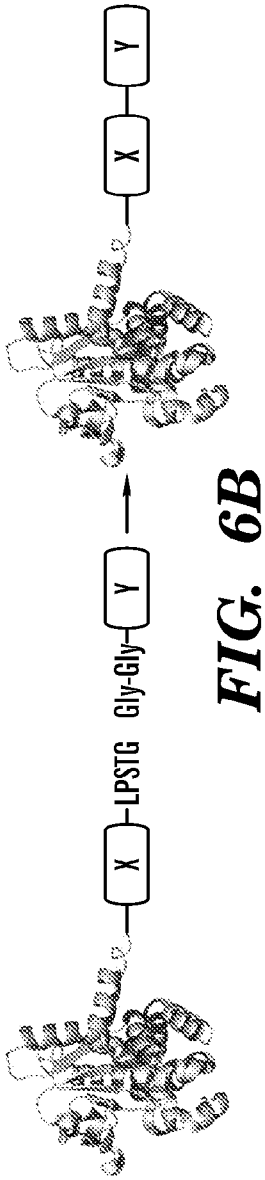
Figure 7:
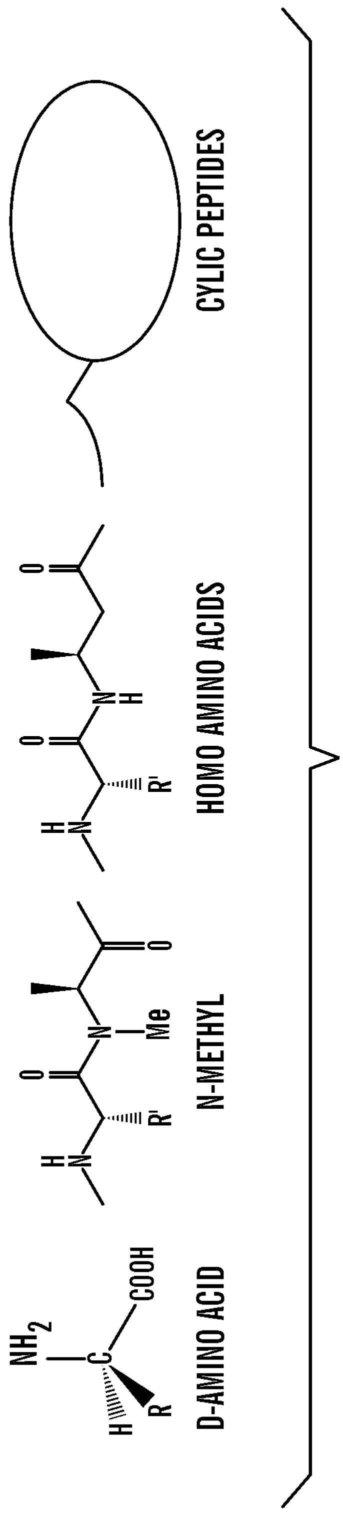
FIG. 7 shows shorthand of the chemical entities attached to LFN and found to translocate through PA pore when investigated in planar lipid bilayers and or CHO-K1 cells.

We have developed a technology for the efficient delivery of non-natural chemical entities, i.e. entities comprising modified amino acids, entities not naturally produced by the eukaryotic cells or the like, to the cytosol of eukaryotic cells. The technology relies on the use of the N-terminal domain of lethal factor and protective antigen which when added to cells acts to form a nanomachine that delivers functional bioactive molecules to the cytosol of a target cell. The LFN delivery module is shown in FIGS. 4A-4C. The chemical entities are covalently attached, preferably to the C-terminus of LFN or a functional fragment or modified fragment thereof by native chemical ligation or by the transpeptidase, sortase A (FIG. 6A-6B). The delivery process is highly efficient in that nanomolar concentrations of the reagents are used. For example, we have shown that D-peptide segments, cyclic peptides, and other chemical entities can be delivered using this platform (FIG. 7).

The methods we have developed solve the longstanding problem and unmet need of delivering stable, non-immunogenic, bioactive protein molecules to the cytosol of mammalian cells for example, for therapeutic purposes.

The delivery of D-peptide segments to the cytosol of a cell via a bacterial toxin pore is unprecedented. This is because one would not have expected to use a naturally existing transport system, such as the bacterial toxin pore for delivery of other than naturally occurring proteins or peptides. This is because most protein-protein interactions are based on highly specific stereochemical arrangements which typically determine the exquisite function of proteins. Placing a D-peptide segment in the present system would have been expected to have disrupted this process. Active D-peptide or D-protein moieties in the intracellular compartment of a cell maybe advantageous in that the mirror image form can be evolved to have high affinity and specificity for a particular target just as L-proteins. However, D-moieties are stable against natural occurring proteases and are more likely to be non-immunogenic.

Cyclic peptides are another class of molecules that can be delivered to the cytosol by use of bacterial toxin, such as anthrax toxin pore. Cyclic peptides are widely used by nature and mankind as biological agonists and antagonists. Cyclic peptides have superior pharmacokinetic profiles because they are more stable than the linear counterpart. In addition, cyclic peptides are rigid and can be engineered to have high affinity and specificity for most protein targets.

Many pathogenic bacteria have evolved protein machinery that efficiently delivers potent enzymes to the cytosol of mammalian cells. Some infectious bacteria secrete protein toxins that reach the cytosolic compartment of host cells and disrupt homeostasis. A major class of bacterial toxins, termed AB toxins, use a transporter protein (B or binding unit) that actively translocates enzymes (A unit) into cells. Examples of AB toxins include botulinum neurotoxin, anthrax toxin, diphtheria toxin, shiga toxin, shiga like toxin, exotoxin A, and cholera toxin. Due to the similar mechanism of action between all of these toxins, all these toxins are contemplated to work in the various aspects of the present invention. The A and B components of these and a variety of other toxins are well known.

Bacterial toxins frequently have two functionally distinct moieties, termed A and B. The "A" component is usually the "active" portion, and the "B" component is usually the "binding" portion. Thus, the A moiety or component contains the catalytic activity, while the B moiety or component possesses determinants needed for the cytoplasmic delivery of the A moieties into target cells. These delivery determinants include receptor binding activity, and often, but not always, membrane penetration activity. Many bacterial toxins, such as diphtheria toxin, contain both moieties within a single polypeptide. Anthrax toxin, by contrast, is a member of the so-called binary toxins, a class in which the A and B functions inhabit separate proteins. Although separate, the proteins having the A and B functions interact during the intoxication of cells. Anthrax toxin uses a single B moiety, protective antigen (PA; 83 kDa), for the delivery of two alternative A moieties, edema factor (EF; 89 kDa) and lethal factor (LF; 89 kDa) into the cytoplasm.

The AB family of toxins is a large family of toxins. The structure shown in this application with respect to anthrax toxin is contemplated to be applicable to this entire class of AB toxins. Specifically useful toxins include, but are not limited to botulinum neurotoxin, anthrax toxin, diphtheria toxin, shiga toxin, shiga like toxin, exotoxin A, and cholera toxin.

Table 1 below includes some examples of the known structures of bacterial toxins. Given the structure of the toxin and the description provided herein, a skilled artisan can create a variety of different toxin delivery vehicles.

TABLE 1

Examples of bacterial toxin structures

| Toxin | Arrangement of subunits A and B in the toxin |
|---|---|
| Cholera toxin | (A-5B) wherein subunits A and B are synthesized separately and associated by noncovalent bonds; 5B indicates that the binding domain is composed of 5 identical subunits. |
| Diphtheria toxin | (A/B) wherein subunit domains A and B are of a single protein that may be separated by proteolytic cleavage. |
| *Pertussis* toxin | (A-5B) wherein subunits A and B are synthesized separately and associated by noncovalent bonds; 5B indicates that the binding (B) domain is composed of 5 identical subunits. |
| *E. coli* heat-labile toxin LT | (A-5B) wherein subunits A and B are synthesized separately and associated by noncovalent bonds; 5B indicates that the binding domain is composed of 5 identical subunits. |
| Shiga toxin | (A/5B) wherein subunit domains A and B are of a single protein that may be separated by proteolytic cleavage; 5B indicates that the binding domain is composed of 5 identical subunits. |
| *Pseudomonas* Exotoxin | A (A/B) wherein subunit domains A and B are of a single protein that may be separated by proteolytic cleavage. |
| Botulinum toxin | (A/B)subunit domains are of a single protein that may be separated by proteolytic cleavage |
| Tetanus toxin | (A/B) wherein subunit domains A and B are of a single protein that may be separated by proteolytic cleavage |

TABLE 1-continued

| Examples of bacterial toxin structures | |
|---|---|
| Toxin | Arrangement of subunits A and B in the toxin |
| Anthrax toxin Lethal Factor | (A2 + B) wherein subunits synthesized and secreted as separate protein subunits that interact at the target cell surface |
| *Bordetella pertussis* AC toxin | (A/B)subunit domains are of a single protein that may be separated by proteolytic cleavage |
| *Bacillus anthracis* EF | (A1 + B) wherein subunits synthesized and secreted as separate protein subunits that interact at the target cell surface |

For example, anthrax lethal toxin comprises an enzymatic moiety, lethal factor (LF) a 90 kDa zinc protease, and a receptor-binding/pore-forming moiety, termed protective antigen (PA; 83 kDa). The protein components of anthrax lethal toxin and the cellular entry process are shown in FIG. 1. PA binds to host cell surface receptors and is cleaved by a furin-family protease to an active 63 kDa PA form (PA63) that self-assembles into a ring-shaped heptamer or octamer to form a receptor-bound prepore. The PA63 prepore binds up to three or four molecules of lethal factor forming complexes that are then endocytosed. Upon acidification of the endosome, protective antigen prepore undergoes a conformational rearrangement to form a membrane-spanning, ion-conductive pore, which transports lethal factor from the endosome to the cytosol. LFN, the N-terminal domain of lethal factor, has nanomolar binding affinity for the pore, and this domain alone can be used for translocation of chemical moieties.

Moreover, we have shown that a small positively charged peptide segments that mimic LFN can be used to aid in translocating these molecules through PA pore. These mimics may be composed of at least one non-natural amino acid (see, e.g., FIG. 2A).

Another example is the diphtheria toxin produced by *Corynebacterium diphtheriae*. Diphtheria toxin is a bacterial exotoxin of the A/B prototype. It is produced as single polypeptide chain with a molecular weight of 60,000 daltons. The function of the protein is distinguishable into two parts: subunit A, with a molecular weight of 21,000 daltons, contains the enzymatic activity for inhibition of elongation factor-2 involved in host protein synthesis; subunit B, with a molecular weight of 39,000 daltons, is responsible for binding to the membrane of a susceptible host cell. The B subunit possesses a region T (translocation) domain which inserts into the endosome membrane thus securing the release of the enzymatic component into the cytoplasm. Thus, the T-region of the B subunit in diphtheria toxin can be modified similarly as shown for the B unit of the LF in FIG. 2A.

The term "intracellularly acting bacterial toxin" referred to herein is intended to encompass any and all bacterial toxins and fragments thereof which can bind protective antigen, and which under natural circumstances are transported into cytosol. Examples of such toxins include anthrax lethal toxin, and its N-terminal fragment (LFN), cholera toxin and diphtheria toxin. Protein toxins, notably those that act intracellularly (with regard to host cells), consist of two components: one component (subunit A) is responsible for the enzymatic activity of the toxin; the other component (subunit B) is concerned with binding to a specific receptor on the host cell membrane and transferring the enzyme across the membrane. The enzymatic component is not active until it is released from the native (A+B) toxin. Isolated A subunits are enzymatically active but lack binding and cell entry capability. Isolated B subunits may bind to target cells (and even block the binding of the native toxin), but they are nontoxic.

There are a variety of ways that toxin subunits may be synthesized and arranged: A+B indicates that the toxin is synthesized and secreted as two separate protein subunits that interact at the target cell surface; A–B or A–5B indicates that the A and B subunits are synthesized separately, but associated by noncovalent bonds during secretion and binding to their target; 5B indicates that the binding domain of the protein is composed of 5 identical subunits. A/B denotes a toxin synthesized as a single polypeptide, divided into A and B domains that may be separated by proteolytic cleavage. Table 1 sets forth examples of intracellularly acting bacterial toxins.

As used herein, the term "mimetic" refers to a compound that structurally and/or functionally mimics a target compound. Accordingly, an "A component mimetic" refers to a compound that mimic the structure and/or function of an A component.

As used herein, the term "surrogate" refers to a compound that can be used structurally and/or functionally in place of a target compound. Accordingly, an "A component surrogate" or "surrogate A component" which are used interchangeably, refer to a compound that can emulate the structure and/or function of an A component. Examples of A component surrogates are charged L and D amino acid stretches, such as SSv3 or SSv4 which have a repeating sequence of a positively charged Lysine (K) and a negatively charged glutamic acid (E). Thus, for example, variations of SSv3 are peptides that begin with E and end with E instead of beginning with K and ending with K as shown for the SSv3 sequence. Other variants include other basic/acidic amino acids. Thus, in one variant, the E in SSv3 can be replaced by another negatively charged amino acid, D (aspartic acid), and K can be replaced by other positively charged amino acids, such as Arginine (R) or Histidine (H). Similar modifications can be performed for any other charged bacterial toxin domain that functions in transporting the toxin enzyme through the cell membrane.

Accordingly, in some aspects of all the embodiments of the invention the A component surrogate is selected from N-terminal unstructured, highly charged segments of bacterial toxin A parts that are 17-29, 10-35, or 15-30 amino acid residues long wherein the amino acids alternate between positively and negatively charged residues ("positively charged amino acid-negatively charged amino acid-positively charged amino acid-negatively charged amino acid . . . " or as "negatively charged amino acid-positively charged amino acid-negatively charged amino acid-positively charged amino acid . . . "), and wherein the negatively charged amino acids are selected from E and D, or D-amino acid isoforms of the same, and the positively charged amino acids are selected from K, R, and H, or D-amino acid isoforms thereof.

We have shown that N terminal unstructured segment of LF does not adopt a conformation that interacts with the pore in a stereospecific manner during protein translocation. Rather, it appears to function by delivering a segment of highly charged amino acids to the pore to assist the protein translocation through the pore. Accordingly, and without wishing to be bound by a theory, we believe that this property is a characteristic of the entire protein (notwithstanding that the globular portion of LFN binds stereospecifically to sites at the mouth of the pore before it unfolds as a prelude to translocation).

Similarly, any N-terminal unstructured region of any other bacterial toxin can be considered to be similarly flexible in the sense that the amino acids of those segments can be changed to a stretch of highly charged amino acids, including D amino acids. Thus, for example, similar change to a simple peptide comprising basic residues, such as K and E (see, e.g., FIG. 2A, SSv3 and SSv4) can be made to any other toxin protein that is made to assist delivery of the peptides into a cell.

Table 2 shows examples of other toxin sequences which can be used in the methods of the present invention.

| Toxin | SEQ ID NO: | Amino acid a bioactive molecule can be attached |
|---|---|---|
| Diphtheria toxin | 4 | 1 of SEQ ID NO: 4 |
| Shiga toxin | 5 | 1 of SEQ ID NO: 5 |
| Shiga toxin B part | 6 | — |
| Exotoxin A | 7 | 1 of SEQ ID NO: 7 |
| Cholera toxin A1 fragment | 8 | 1 of SEQ ID NO: 8 |
| Cholera toxin A2 fragment | 9 | — |
| Cholera toxin B fragment | 10 | — |

In some aspects of all the embodiments of the invention, the bioactive moieties or molecules with at least one non-natural component are selected from peptides and proteins comprising one or more D-amino acids, N-methyl comprising peptides/proteins, homo amino acid comprising peptides/proteins, and cyclic peptides, side-chain modified amino acids containing groups composed of fluorine, bromine, iodine, biotin, azide, alkene, alkyne, glycan, lipid, phosphate, polyethylene glycol, thiol, thioester, keto acid, samarium, lanthanum, terbium, and various fluorophores. In some aspects of all the embodiments of the invention the bioactive moieties of the invention can be selected from backbone modifications, such as reduced isosteres, N-methyl amides, circular peptides, ether peptides, and hydrocarbon linkers, conformation locked peptides and proteins including stapled peptides and cyclic proteins, as well as peptidomimetics including peptoids and beta-peptides.

In some aspects, the methods, fusion molecules, compositions and kits of the invention are directed to delivering bioactive molecules to an eukaryotic cell, wherein the bioactive molecule is a natural molecule that is not naturally cell permeable, including chiral modifications, such as D-amino acids.

In some aspects of all the embodiments of the invention, deoxyribonucleic acids (DNA), ribonucleic acids (RNA), peptide nucleic acids (PNA) and only L-amino acid containing natural peptides and proteins are specifically excluded.

Figure 2A:
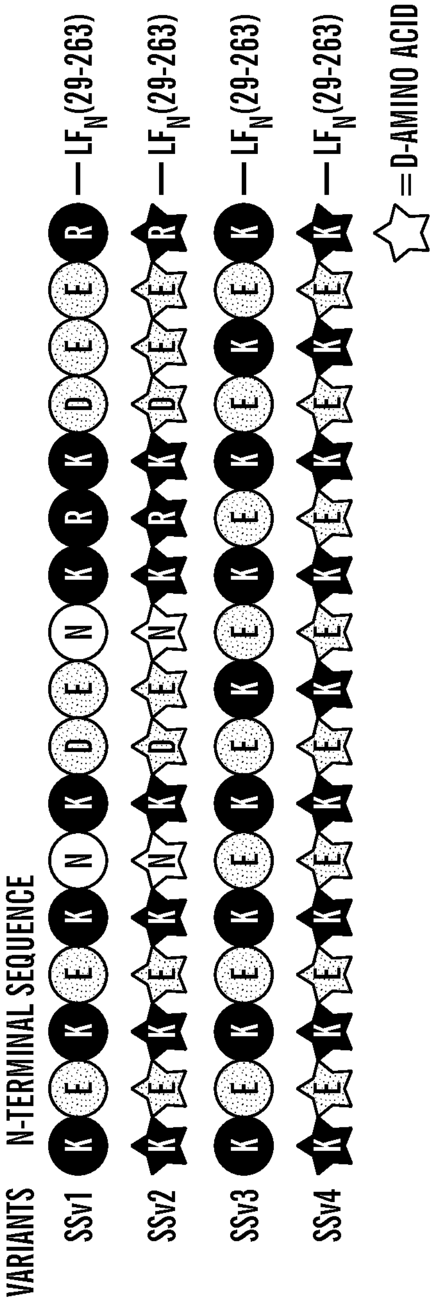
FIGS. 2A-2E show stereochemical and charge effects on the interaction of the LFN N-terminus with PA pore.
Figure 2B:
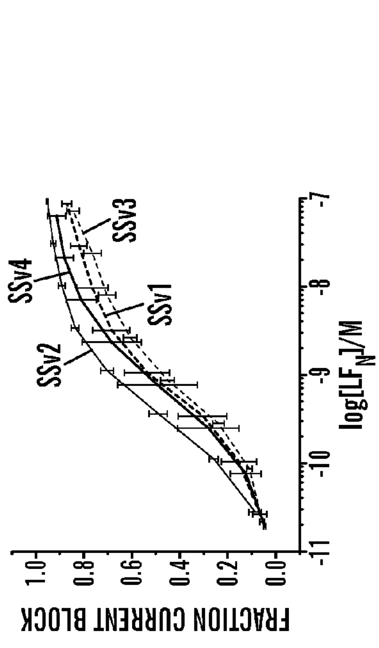
Figure 2C:
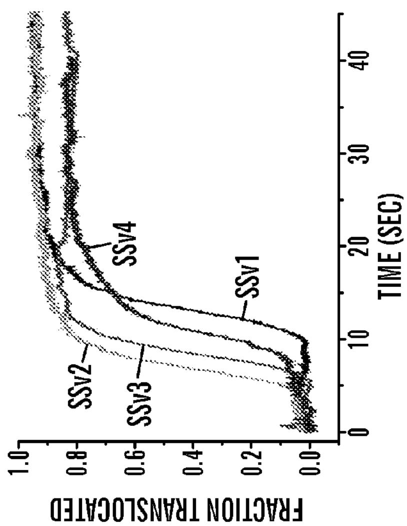
Figure 2D:
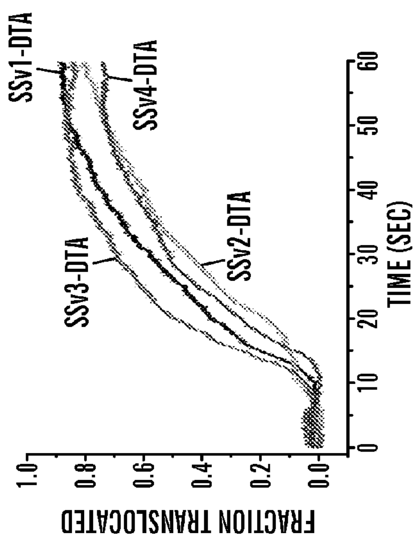

In some aspects of all the embodiments of the invention, when using A-component selected from the peptides set forth in FIG. 2A, one can also deliver DNA, RNA, PNA and only L-amino acid containing natural peptides and proteins. Accordingly, the invention also provides aspects wherein the methods, compositions and kits are directed to delivery of not only the modified and non-natural peptides or proteins but also DNA, RNA, PNA and only L-amino acid containing natural peptides and proteins using bacterial toxin components wherein the unstructured, highly charged domain of the A part has been replaced by a highly charged surrogate A part, such as the sequences for SSv3 and SSv4 set forth in FIG. 2A.

While natural toxin systems have been used in delivering nucleic acids and natural protein fragments into cells (see, e.g., U.S. Patent Application Publication No. 2003-0202989), to our knowledge, no one has previously proposed using this system for delivery of molecules other than naturally occurring ones because of expected stereochemical, steric, and binding problems. In addition, issues related to attaching such non-natural molecules to the bacterial toxins was a problem. Moreover, the modified A fragments described herein examples of which are set forth, e.g., FIG. 2A, have not been previously described. For the first time we propose using the highly charged surrogate A parts for the delivery of proteins and peptides to the eukaryotic cells.

We have discovered that bacterial toxin B components, in general, may be used to deliver bioactive moieties into the cytosol of the cells when the bioactive moiety is attached to the A-component or a surrogate A component of the bacterial toxin. When we attached a bioactive peptide or protein comprising non-natural amino acids, such as D-amino acids to the nontoxic PA-binding domain of LF (LFN), we discovered that the fusion protein thus formed passes through the pore into the cytosol of a cell.

We discovered that we can covalently attach a bioactive moiety to the PA-binding domain of a bacterial toxin A component either using native chemical ligation methods or sortase tagging (see, e.g., Thomas Proft, Sortase-mediated protein ligation: an emerging biotechnology tool for protein modification and immobilization. Biotechnol Letters 32:1-10, 2010).

In native chemical ligation a peptide containing a C-terminal thioester reacts with another peptide containing an N-terminal cysteine residue, in the presence of an added thiol catalyst. In a freely reversible first step, a transthioesterification occurs to yield a thioester-linked intermediate; this intermediate rearranges irreversibly under the usual reaction conditions to form a native amide ('peptide') bond at the ligation site. Native chemical ligation of unprotected peptide segments was developed in the laboratory of Stephen Kent at The Scripps Research Institute in 1994. For references, see, e.g., Dawson P E, Muir T W, Clark-Lewis I, Kent, SBH (1994). "Synthesis of Proteins by Native Chemical Ligation". Science 266: 776-779; Muir T W, Sondhi D, Cole P A (1998). "Expressed Protein Ligation: A General Method for Protein Engineering". Proc. Natl. Acad. Sci. USA 95: 6705-6710; and Nilsson B L, Soellner M B, Raines R T (2005). "Chemical Synthesis of Proteins". Annu. Rev. Biophys. Biomol. Struct. 34: 91-118.

For example, PA may be purified, for example, from the Sterne strain of *Bacillus anthracis* or synthesized by other known means. In *Bacillus anthracis*, the gene for PA is located on a plasmid referred to as pXO1 (Milne et al., 1994, J. of Biol. Chem. 269(32):20607-20612). PA63 can be substituted for full-length PA. This is the preferred approach where the target cell lacks the protein required to cleave full length PA into PA63. The PA63 fragment may be purified from trypsin-treated PA by anion exchange chromatography (Milne et al., 1994, supra). PA encoding gene has been cloned and sequenced (Vodkin, et al., 1983, Cell 34:693-697) and may be used to obtain purified PA polypeptide.

While the invention is not limited by cell type, for PA-dependent methods the cell types targeted must express a functional PA receptor. To date all cell types tested have been able to bind PA (Leppla, S. H. review: Leppla, S. H. 1991. The Anthrax Toxin Complex in (J. E. Alouf, J. H. Freer, eds. Sourcebook of Bacterial Protein Toxins, Academic Press, London).

We contemplate that the delivery methods and platform we have described here can be used to deliver any protein comprising D-amino acids and also small D-proteins.

We further envision that the methods can be used to deliver any kind of chemical group that can be attached to the toxin delivery system into a cell.

We also contemplate that we can target specific cell types by modifying the receptor binding domains of the B toxin fragment.

Moreover, we contemplate that a small peptide segment that mimics LFN can be used to aid in translocating these molecules through PA pore.

Using this platform, we can carry out combinatorial screening inside the cytosol of a mammalian cell and if so what is the best screening approach.

Moreover, analogues of bacterial toxins such as diphtheria toxin and cholera toxin can be used to deliver the novel chemical entities. Thus, in one embodiment, the invention provides a method of treating a subject by contacting cells of the subject either in vivo or ex vivo with a composition comprising a chemical entity intended to the delivered into the cell of the subject with a fusion molecule comprising the component A or a surrogate A component attached to the chemical entity.

The composition can be delivered in a pharmaceutically acceptable carrier. As used herein, the terms "pharmaceutically acceptable refers to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

The chemical entity can be covalently attached to the bacterial toxin A part.

The contacting can be performed in vivo, or ex vivo or in vitro. For the ex vivo application, the cells are typically obtained from the subject for which the therapy is intended, i.e., the cells are autologous. In some aspects of all the embodiments of the invention, also heterologous cells can be used.

The term "subject" as used herein and throughout the specification is intended to include organisms with eukaryotic cells, including mammals, such as humans and domestic animals, laboratory animal models, including rodent, canine, and primate models.

We can also use this technology to elicit specific immune responses to post translationally modified proteins such as phosphopeptides and glycopeptides. Thus, in one embodiment, the invention provides a method of antibody production by contacting a model animal or cells derived from a model animal with a fusion comprising a post translationally modified protein, such as a phosphopeptide or a glycopeptide, fused with an A component or surrogate A component of a bacterial fusion protein and further contacting the model animal or cells derived from the model animal with a B component corresponding to the A component. The method optionally comprises a step of screening the blood or yolk if the model animal is a fowl, such as a chicken for an antibody that is specific for the desired post translationally modified protein. In some aspects, the method further comprises isolating the antibody.

We can also use various protease cleavage sites in the system to allow release of the agents, such as the chemical compounds from the delivery vehicle.

The B component corresponding to the A component used herein and throughout the specification refers to the specific bacterial toxin parts examples of which are shown, e.g., in Table 1.

A comprehensive list of amino acid or nucleotide sequences for the A and B parts are too numerous to list, and the person of skill in the art is referred to the readily available publicly accessible databases. Modifications to such sequences can be made using basic amino acid synthesis methods or recombinant nucleotide technology depending on the extent of the modifications needed.

Moreover, the methods can be used to effectively and efficiently deliver, e.g., Zn finger proteins or stem cell transcription factors or single chain antibodies to cells either in vitro or in vivo. In one example, the system of delivering immunotherapy for immunotherapy for prostate cancer in which the methods of the invention are used to deliver prostate cancer antigens to dendritic cells which are then transferred back into the patient. The methods allow us to do an intranodal injection with the lethal toxin delivery system. Thus, in one embodiment, the invention provides a method of delivering immunotherapy for prostate cancer comprising administering to a subject diagnosed with prostate cancer, and optionally screened as a suitable target subject for immunotherapy, a fusion peptide comprising a prostate cancer antigen covalently linked to a surrogate A part of a bacterial toxin. In one embodiment, the subject is administered dendritic cells that have been contacted with the fusion peptide. In one embodiment, the administering is intranodal.

In some embodiments, the invention provides a method comprising contacting an eukaryotic cell, in vivo or in vitro, with a peptide or protein that have been covalently attached to a surrogate A part of a bacterial toxin. In some embodiments the cells are dendritic cells.

Anthrax lethal toxin exemplifies one among many systems evolved by pathogenic bacteria for transporting proteins across membranes to the cytosol of mammalian cells. [1] The transported proteins—so called effector proteins—are enzymes that modify intracellular substrates, perturbing mammalian metabolism in ways that benefit the bacteria at the expense of the host. Anthrax lethal toxin is an ensemble of two large soluble proteins: the Lethal Factor (LF, 90 kDa), a zinc protease,[2] and Protective Antigen (PA; 83 kDa), a receptor-binding/pore-forming protein.[1] PA binds to receptors[3] on host cells and is cleaved by a furin-family protease [4] to an active 63 kDa form (PA63),[5] which self-assembles into ring-shaped heptameric[6] and octameric[7] oligomers, termed prepores. The prepores bind LF, forming complexes that are then endocytosed and delivered to the endosome. There, acidification induces the prepore moieties to undergo conformational rearrangement to membrane-spanning pores. [1] The pores then transport bound LF across the membrane to the cytosol, where it inactivates selected target proteins.[8] Edema Factor (EF), the enzymatic moiety of anthrax edema toxin,[9] is transported to the cytosol by a similar mechanism. [1]

LF binds to PA63 pores via its N-terminal domain, termed LFN, orienting the protein's N-terminal unstructured, highly charged segment (~29 residues) at the pore entrance. This unstructured segment is believed to enter the pore lumen and interact with the Phe clamp,[10] a structure formed by the Phe427 side chains, thereby blocking ion conductance and initiating N- to C-terminal threading of the polypeptide through the pore (FIG. 1).[11] Removal of the first 12 residues (i.e. residues AGGHGDVGMHVK (SEQ ID NO: 11)) of this unstructured segment was found to have little effect on translocation, but truncations of more than 27 residues altered the ability of LFN to block ion conductance and to be translocated through the pore.[11-12] Accordingly, in some aspects of all the embodiments of the invention, the N-terminal domain set forth in FIG. 1A can be shortened from its N-terminal end by 1, 2, 3, 4, 5, 6, 7, 8, 9, 10, 11 or 12 residues, for example from 1-12 residues, 1-6, 2-6, 2-12, 2-10, 5-10, or 5-12 residues.

In the current study, to probe how structural and electrostatic changes in translocation-competent polypeptides affected translocation, we used native chemical ligation [13] to prepare truncated variants of LFN (residues 12-263 of the native domain), in which residues 12-28 were replaced by synthetic peptides (FIG. 1). We also fused each of the LFN variants to the N terminus of the catalytic domain of diphtheria toxin (DTA), to permit the effects of the modifications to be measured on mammalian cells. DTA blocks protein synthesis when introduced into the cytosol of these cells.[14]

Figure 1A:
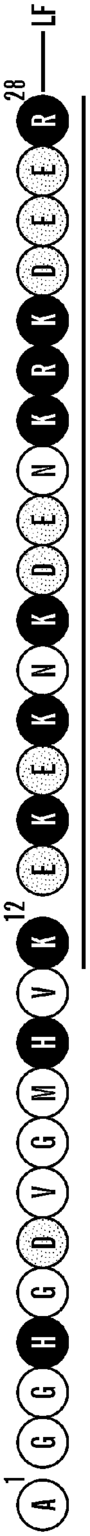
FIGS. 1A-1C show interaction of the N terminus of LF with PA pore.
Figure 1C:
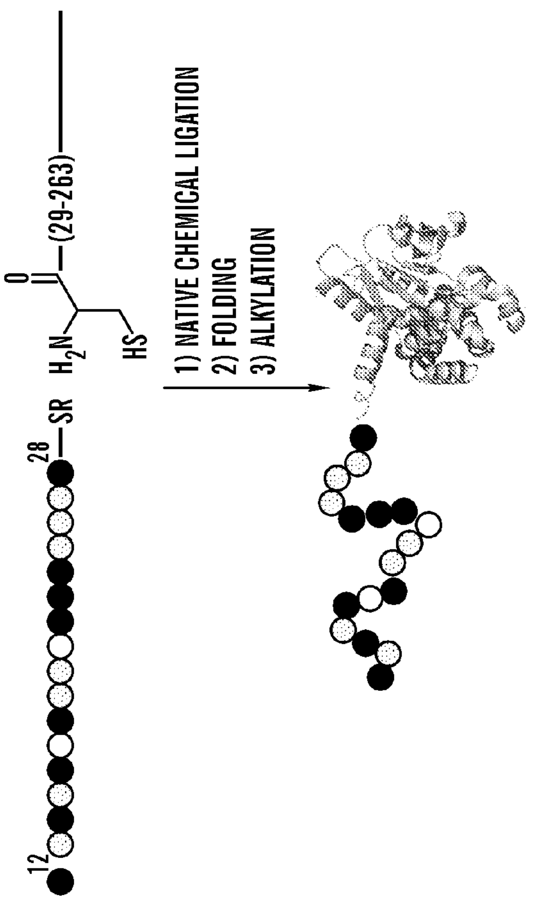
Figure 1B:
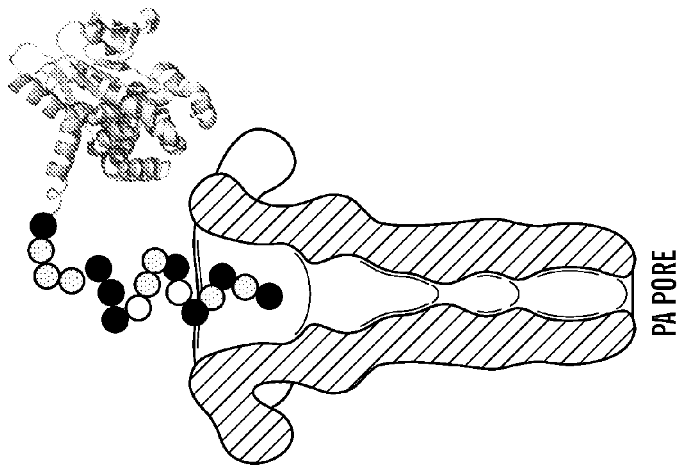

FIGS. 1A-1C demonstrate the interaction of the N terminus of LF with PA pore. FIG. 1A shows the N-terminal 28 amino acid residues of LF, with the highly charged region investigated in this report underlined. FIG. 1B is an illustration of the N-terminal binding domain of Lethal Factor, LFN (1-263) (SEQ ID NO: 19), yellow, bound to PA pore. The pore structure was reconstructed from single-pore images obtained by electron microscopy.[18] The black (basic), dotted (negative), and white (neutral) circles represent the unstructured N-terminal stretch of LF(12-28), which was not present in the X-ray structure of LF (PDB 1J7N). FIG. 1C shows the semisynthesis strategy used to prepare LFN constructs with modifications in the (12-28) amino acid stretch.

Six semisynthetic variants of LFN, SSv1-SSv6, were prepared. [12] Briefly, LFN(12-28)αthioesters were synthesized by manual Boc in-situ neutralization solid phase peptide synthesis[15] and purified by RP-HPLC. N29C-LFN(29-263) was prepared from a His6-SUMO-N29C-LFN(29-263) protein ("His6" disclosed as SEQ ID NO: 12) fusion recombinantly expressed in *E. coli*. Standard ligation conditions were used to couple the LFN(12-28)αthioester and N29C-LFN (29-263), yielding the reaction product N29C-LFN(12-263) (FIG. 1C). N29C-LFN(12-263) was alkylated with 2-bromoacetamide to give N2949-LFN(12-263) (ΨQ=pseudohomoglutamine). LFN-DTA variants were prepared by use of recombinant N29C-LFN(29-263)-DTA [C186S]. Each analogue was characterized by analytical RP-HPLC, high-resolution MS, and circular dichroism. The circular dichroism spectra of all variants were similar to that of LFN(12-263), implying that the variants were correctly folded. Accordingly, in some aspects of all the embodiments of the invention, one or more of the variants shown in FIG. 2A is used in the methods, compositions and kits of the invention.

Figure 2E:
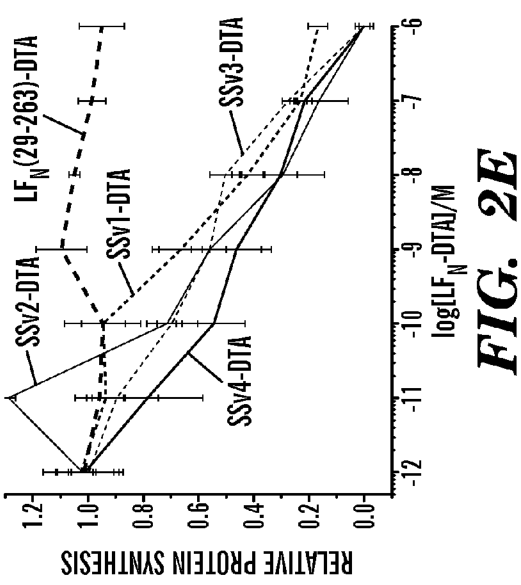
Figure 3A:
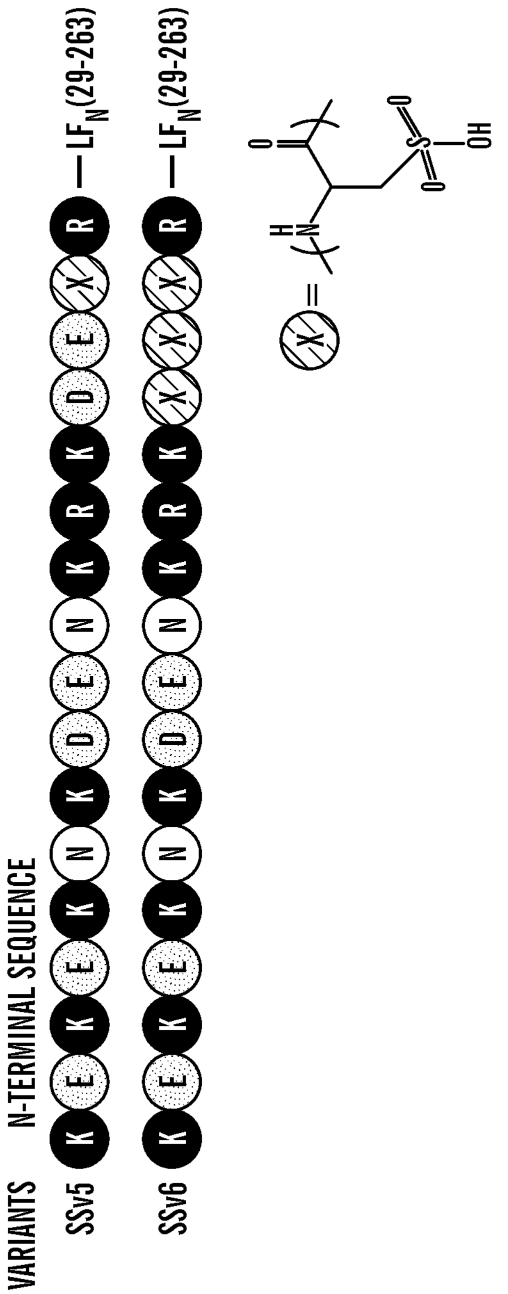
FIGS. 3A-3E show translocation of LFN variants through PA pore is hindered by cysteic acid.
Figure 3B:
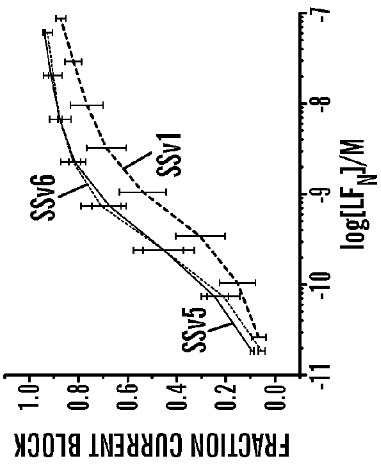
Figure 3C:
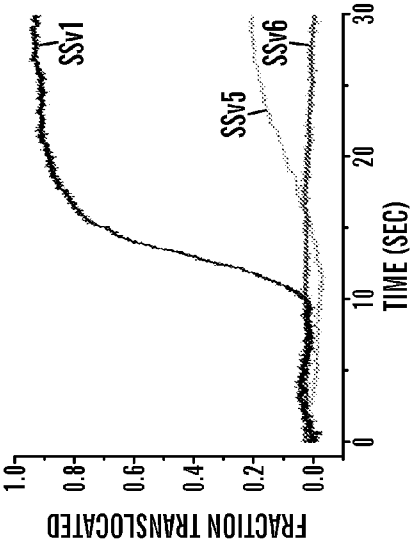
Figure 3D:
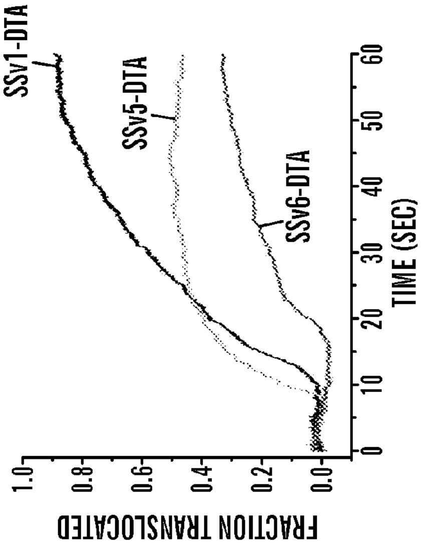
Figure 3E:
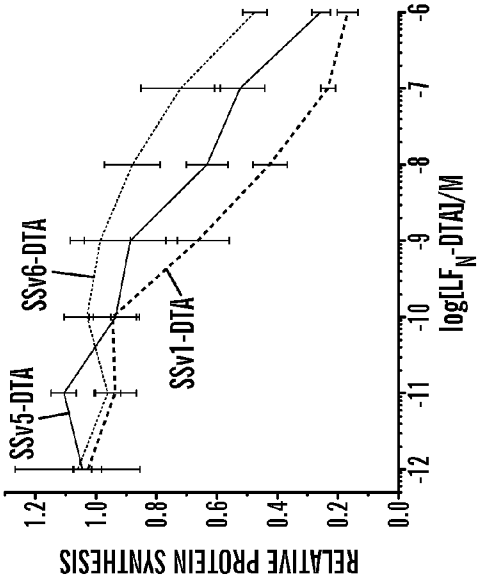

To investigate the possibility that chirality of amino acids could affect translocation, we prepared SSv2, a variant of wild-type LFN in which the residue 12-28 peptide was synthesized from D amino acids (FIG. 2). No significant differences were observed between the D and L variants of LFN in ability to inhibit ion conductance through PA pores formed in planar phospholipid bilayers (FIG. 2B) or to translocate through those pores in response to a transmembrane pH gradient (cis pH 5.5; trans pH 7.5) (FIG. 2C).[16] Further, there was no difference between the SSv2-DTA and the wild-type SSv1-DTA fusion proteins in ability to translocate in-vitro or to inhibit protein synthesis in CHO-K1 cells. Accordingly, in some aspects of all the embodiments of the invention, variants with one or more D-peptides in the N-terminal sequences set forth in FIG. 2A are used. In some embodiments 1-17, 2-17, 3-17, 4-17, 5-17, 6-17, 7-17, 8-17, 9-17, 10-17, 11-17, 12-17, 13-17, 14-17, 15-17, 16-17, or 1, 2, 3, 4, 5, 6, 7, 8, 9, 10, 11, 12, 13, 14, 15, 16, or 17 of the N-terminal amino acids set forth in FIG. 2A are D amino acids. Similar substitutions can be made in any other bacterial toxin A-domain, particularly to the pore-binding N-terminal domain of the A domain. Sequences to these domains are widely available in the databases and can thus be constructed FIGS. 2A and 2B show stereochemical and charge effects on the interaction of the LFN N-terminus with PA pore. FIG. 2A shows chemical framework of SSv1-SSv4. FIG. 2B shows the fraction ion conductance block of PA pore by LFN variants at ΔΨ=20 mV (ΔΨ=Ψcis−Ψtrans, where Ψtrans≡0). For the procedure used to determine the fraction ion conductance block shown in FIG. 2 and FIG. 3 see the supplementary information. Each blocking experiment was repeated three times. FIG. 2C shows acid triggered translocation of LFN variants through PA pore in response to a pH gradient of −2 units (cis pH 5.5; trans pH 7.5) at ΔΨ=20 mV. FIG. 2D shows translocation of LFN-DTA variants through PA pore in response to a pH gradient of −2 units (cis pH 5.5; trans pH 7.5)

at $\Delta\Psi$=20 mV. FIG. 2E shows fraction protein synthesis inhibition by LFN-DTA variants in CHO-K1 cells. LFN-DTA variants were incubated at the indicated concentration for 15-17 minutes at 37° C. and 5% CO2. Then, 3H-leucine was added, and after 1 hour the amount of tritium incorporated into cellular protein was measured. The data shown are the average of three experiments.

The residue 12-28 sequence of native LFN underlined in FIG. 1A is comprised of 8 basic (black circles), 7 acidic (dotted circles), and 2 neutral (white circles) residues (FIG. 1A). When we replaced this segment with a simple sequence of alternating basic and acidic residues (9 Lys and 8 Glu) (FIG. 2*a*), generating variant SSv3, we found no significant change in the ability of the protein to block ion conductance or to be translocated. Also, the corresponding DTA fusion protein, SSv3-DTA, behaved essentially identically to the controls in the translocation assay in bilayers and the cytotoxicity assay in cell culture. Further, SSv4 and SSv4-DTA, having the same alternating Lys/Glu sequence, but synthesized with D amino acids, showed no differences in activity from SSv3 and SSv3-DTA, respectively.

Translocation through PA pores formed in planar bilayers can be driven by applying a transmembrane pH gradient (low pH cis, higher pH trans).[16] This finding, together with the fact that the lumen of the pore is negatively charged and discriminates against the passage of anions, suggested a charge state-dependent Brownian ratchet mechanism.[10,16-17] According to this model a negative electrostatic barrier within the pore serves to retard the passage of acidic residues of a translocating polypeptide when their side chains are deprotonated. Protonation renders the side chains neutral, allowing the polypeptide to pass the barrier by random thermal motion. Once the residue has passed, deprotonation renders the side chain once again negative, hindering back diffusion across the barrier. A proton gradient across the membrane would therefore be expected to impose directionality upon the thermal motion, driving translocation by virtue of the greater probability of acidic residues being in a protonated state at lower pH values.

As a test of this hypothesis we prepared variants of LFN (12-263) in which selected acidic residues were replaced with the unnatural amino acid, cysteic acid, which has a negatively charged side chain (pKa 1.9) that protonates only at pH values below the physiological range. In SSv5 we replaced Glu27 alone with cysteic acid, and in SSv6, we replaced three sequential acidic residues: Asp25, Glu26, and Glu27 (FIG. 3). Both constructs bound to PA pores and blocked ion conductance as effectively as the wild-type control. Translocation of SSv5 in response to A pH was strongly inhibited, however, and with SSv6 no translocation was observed. Like SSv5 and SSv6, the corresponding DTA fusion proteins bound to PA pores in planar bilayers and blocked ion conductance effectively. The LFN-DTA variants showed significant levels of translocation activity in bilayers and of cytotoxicity on cells when combined with PA, but the constructs with a single cysteic acid residue were markedly less active than the wild type constructs, and those with three were even less active. Thus, although non-titratable negative charged residues did not abrogate translocation, they clearly served as a barrier to the process.

Semisynthesis provides the opportunity to test the functional consequences of incorporating chemical structures beyond the standard set of L amino acids into proteins. Our finding that the LFN domain functioned equally well when the segment corresponding to residues 12-28 were built from D amino acids as from L amino acids indicates that the N terminal unstructured segment of LF does not adopt a conformation that interacts with the pore in a stereospecific manner during protein translocation. By extension, we suggest that this property is likely to be characteristic of the entire protein (notwithstanding that the globular portion of LFN binds stereospecifically to sites at the mouth of the pore before it unfolds as a prelude to translocation). Further, if polypeptide segments adopt an $\alpha$-helical structure during translocation through the $\beta$-barrel stem of the pore,[16] a left-handed helix must be accommodated as well as a right-handed one. These concepts are consistent with the notions that the protein-translocation pathway must accommodate all side-chain chemistries of the translocating protein and that interactions with the pore cannot be too strong, lest they arrest the translocation process.

Semisynthesis also allowed us to incorporate a non-natural amino acid, L cysteic acid, as a test of the charge state-dependent Brownian ratchet mechanism proposed earlier. [10, 16] The side chain of cysteic acid would be predicted to be negatively charged under the conditions of our experiment and thus retard translocation. The prediction that replacing an existing acidic residue with cysteic acid would inhibit translocation significantly and that replacing three would be even more inhibitory was fulfilled, supporting the proposed mechanism. Another test, in which negatively charged side chains were introduced by derivatization of introduced Cys residues, also gave results supportive of the mechanism.[17a]

Figure 8:
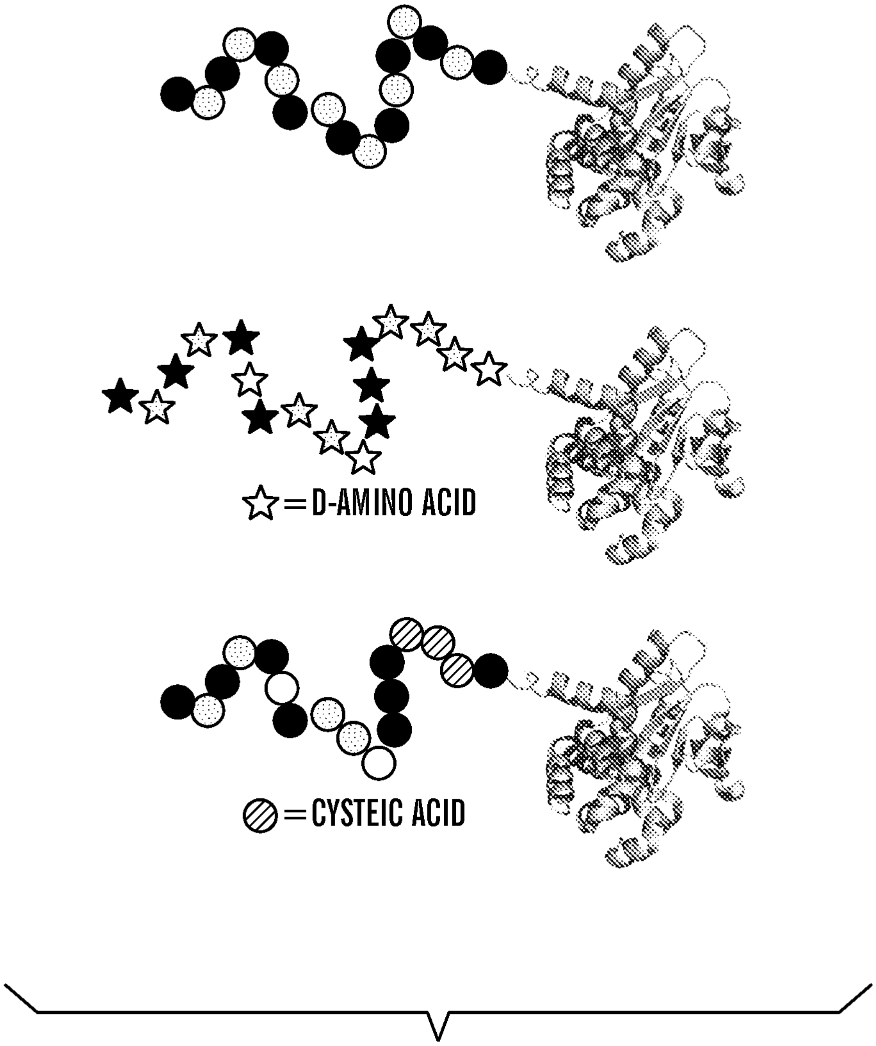
FIG. 8 shows a schematic how we modified the N-terminal domain of the lethal factor of anthrax lethal toxin by semisynthesis to probe protein translocation through the toxin pore. Replacing selected acidic residues with cysteic acid inhibited translocation, whereas replacing a 17-residue segment with D amino acids or an alternating Lys-Glu sequence had no effect. These findings demonstrate a surprising independence of translocation from stereo specificity and strict sequence, and dependence on the charge state of acidic residues.

Protein translocation through the pore. As shown in FIG. 8, we modified the N-terminal domain of the lethal factor of anthrax lethal toxin by semisynthesis to probe protein translocation through the toxin pore. Replacing selected acidic residues with cysteic acid inhibited translocation, whereas replacing a 17-residue segment with D amino acids or an alternating Lys-Glu sequence had no effect. These findings surprisingly demonstrate independence of translocation from stereospecificity and strict sequence, and dependence on the charge state of acidic residues.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited throughout this application and the list of references below are incorporated in their entirety by reference

REFERENCES

The references cited herein and throughout the specification are herein incorporated by reference in their entirety.

[1] J. A. Young, R. J. Collier, Annu Rev Biochem 2007, 76, 243.

[2] a) N. S. Duesbery, C. P. Webb, S. H. Leppla, V. M. Gordon, K. R. Klimpel, T. D. Copeland, N. G. Ahn, M. K. Oskarsson, K. Fukasawa, K. D. Paull, G. F. Vande Woude, Science 1998, 280, 734; b) G. Vitale, R. Pellizzari, C. Recchi, G. Napolitani, M. Mock, C. Montecucco, Biochem Biophys Res Commun 1998, 248, 706.

[3] a) K. A. Bradley, J. Mogridge, M. Mourez, R. J. Collier, J. A. Young, Nature 2001, 414, 225; b) H. M. Scobie, G. J. Rainey, K. A. Bradley, J. A. Young, Proc Natl Acad Sci USA 2003, 100, 5170.
[4] S. S. Molloy, P. A. Bresnahan, S. H. Leppla, K. R. Klimpel, G. Thomas, J Biol Chem 1992, 267, 16396.
[5] K. R. Klimpel, S. S. Molloy, G. Thomas, S. H. Leppla, Proc Natl Acad Sci USA 1992, 89, 10277.
[6] J. C. Milne, D. Furlong, P. C. Hanna, J. S. Wall, R. J. Collier, J Biol Chem 1994, 269, 20607.
[7] A. F. Kintzer, K. L. Thoren, H. J. Sterling, K. C. Dong, G. K. Feld, Tang, II, T. T. Zhang, E. R. Williams, J. M. Berger, B. A. Krantz, J Mol Biol 2009, 392, 614.
[8] L. Abrami, M. Lindsay, R. G. Parton, S. H. Leppla, F. G. van der Goot, J Cell Biol 2004, 166, 645.
[9] S. H. Leppla, Proc Natl Acad Sci USA 1982, 79, 3162.
[10] B. A. Krantz, R. A. Melnyk, S. Zhang, S. J. Juris, D. B. Lacy, Z. Wu, A. Finkelstein, R. J. Collier, Science 2005, 309, 777.
[11] S. Zhang, A. Finkelstein, R. J. Collier, Proc Natl Acad Sci USA 2004, 101, 16756.
[12] B. L. Pentelute, A. P. Barker, B. E. Janowiak, S. B. Kent, R. J. Collier, ACS Chem Biol 2010, 5, 359.
[13] P. E. Dawson, T. W. Muir, I. Clark-Lewis, S. B. Kent, Science 1994, 266, 776.
[14] a) B. R. Sellman, M. Mourez, R. J. Collier, Science 2001, 292, 695; b) B. R. Sellman, S, Nassi, R. J. Collier, J Biol Chem 2001, 276, 8371.
[15] M. Schnolzer, P. Alewood, A. Jones, D. Alewood, S. B. Kent, Int J Pept Protein Res 1992, 40, 180.
[16] B. A. Krantz, A. Finkelstein, R. J. Collier, J Mol Biol 2006, 355, 968.
[17] a) D. Basilio, S. J. Juris, R. J. Collier, A. Finkelstein, J Gen Physiol 2009, 133, 307; b) A. Finkelstein, Philos Trans R Soc Lond B Biol Sci 2009, 364, 209.
[18] H. Katayama, B. E. Janowiak, M. Brzozowski, J. Juryck, S. Falke, E. P. Gogol, R. J. Collier, M. T. Fisher, Nat Struct Mol Biol 2008, 15, 754.

We claim:

1. A method for delivering a bioactive moiety comprising at least one non-natural component into a cell cytosol of an eukaryotic cell comprising contacting the cell with (a) a fusion molecule comprising the bioactive moiety attached to an A component of a bacterial toxin, a functional wild-type or modified fragment thereof, or an A component surrogate or mimetic; and (b) a corresponding B component of the bacterial toxin or a functional fragment thereof, wherein the non-natural component is selected from the group consisting of a peptide or protein comprising one or more D-amino acids.

2. The method of claim 1, wherein the A component surrogate is selected from N-terminal unstructured, highly charged segments of bacterial toxin A parts that are 10-35 amino acid residues long wherein the amino acids alternate between positively and negatively charged residues, and wherein the negatively charged amino acids are selected from E and D, or D-amino acid isoforms of the same, and the positively charged amino acids are selected from K, R, and H, or D-amino acid isoforms thereof.

3. The method of claim 1, wherein the A component of a bacterial toxin, a functional wild-type or modified fragment thereof is selected from amino acid sequences of SEQ ID NO: 14; SSv2; SEQ ID NO: 15; and SSv4.

4. The method of claim 3, wherein the B component is an anthrax protective antigen (PA).

5. The method of claim 1 further comprising a step of attaching the bioactive moiety to the A component of a bacterial toxin or the functional wild-type or modified fragment thereof to form the fusion molecule.

6. The method of claim 5 wherein the fusion molecule further comprises a protease cleavage sequence between the bioactive moiety and the A component of a bacterial toxin or functional wild-type or modified fragment thereof.

7. The method of claim 5 further comprising a step of introducing a protease cleavage sequence into the fusion molecule to allow protease mediated release of the bioactive moiety from the A component after its entry into the cytosol.

8. The method of claim 7, wherein the protease cleavage sequence is selected from a calpain, a caspase, and a cathepsin cleavage sites.

9. The method of claim 8, wherein the protease cleavage sequence is selected from the group consisting of SEQ ID NO: 1, SEQ ID NO: 2 and SEQ ID NO:3.

10. The method of claim 1, wherein the A and B components are selected from the family of intraceullarly acting toxins.

11. The method of claim 10, wherein the A and B components are selected from botulinum neurotoxin, anthrax toxin, diphtheria toxin, shiga toxin, shiga like toxin, exotoxin A, tetanus toxin and cholera toxin.

12. The method of claim 1, wherein the bioactive moiety is attached to the C-terminus or N-terminus of the A component of the bacterial toxin or a functional wild-type or modified fragment thereof.

13. The method of claim 1, wherein the B component is separate from the A component.

14. The method of claim 1, wherein the B component is joined to the A component.

15. The method of claim 1, wherein the attaching is performed using native ligation or sortase mediated protein ligation.

16. The method of claim 1, wherein the contacting is performed in vitro.

17. The method of claim 1, wherein the bioactive moiety comprises an isostere, an N-methyl amide, a circular peptide, an ether peptide, a hydrocarbon linker, a conformation locked peptide, a stapled peptide, a cyclic protein, or a peptidomimetic.

18. The method of claim 1, wherein the bioactive moiety is a D-peptide or a D-protein.

19. The method of claim 1, wherein the bioactive moiety is not a deoxyribonucleic acid (DNA), a ribonucleic acid (RNA), a peptide nucleic acid (PNA), or a natural peptide or protein containing only L-amino acids.

20. A method for delivering a bioactive moiety comprising at least one non-natural component into a cell cytosol of an eukaryotic cell comprising contacting the cell with (a) a fusion molecule comprising the bioactive moiety attached to an A component surrogate of a bacterial toxin; and (b) a corresponding B component of the bacterial toxin or a functional fragment thereof, wherein the A component surrogate is selected from N-terminal unstructured, highly charged segments of bacterial toxin A parts that are 10-35 amino acid residues long wherein the amino acids alternate between positively and negatively charged residues, and wherein the negatively charged amino acids are selected from E and D, or D-amino acid isoforms of the same, and the positively charged amino acids are selected from K, R, and H, or D-amino acid isoforms thereof.

21. The method of claim 20, wherein the A component surrogate is selected from amino acid sequences of SEQ ID NO: 15 and SSv4.

22. The method of claim 21, wherein the B component is an anthrax protective antigen (PA).

23. The method of claim 20 further comprising a step of attaching the bioactive moiety to the A component surrogate to form the fusion molecule.

24. The method of claim 23 wherein the fusion molecule further comprises a protease cleavage sequence between the bioactive moiety and the A component surrogate.

25. The method of claim 23 further comprising a step of introducing a protease cleavage sequence into the fusion molecule to allow protease mediated release of the bioactive moiety from the A component surrogate after its entry into the cytosol.

26. The method of claim 25, wherein the protease cleavage sequence is selected from a calpain, a caspase, and a cathepsin cleavage sites.

27. The method of claim 26, wherein the protease cleavage sequence is selected from the group consisting of SEQ ID NO: 1, SEQ ID NO: 2 and SEQ ID NO: 3.

28. The method of claim 20, wherein the bacterial toxin is selected from the family of intraceullarly acting toxins.

29. The method of claim 28, wherein the bacterial toxin is selected from botulinum neurotoxin, anthrax toxin, diphtheria toxin, shiga toxin, shiga like toxin, exotoxin A, tetanus toxin and cholera toxin.

30. The method of claim 20, wherein the bioactive moiety is attached to the C-terminus or N-terminus of the A component surrogate.

31. The method of claim 20, wherein the B component is separate from the A component surrogate.

32. The method of claim 20, wherein the B component is joined to the A component surrogate.

33. The method of claim 20, wherein the attaching is performed using native ligation or sortase mediated protein ligation.

34. The method of claim 20, wherein the contacting is performed in vitro.

35. The method of claim 20, wherein the non-natural component is selected from the group consisting of a peptide or protein comprising one or more D-amino acids; a peptide or protein comprising one or more N-methyl amino acids; a peptide or protein comprising one or more homo amino acids; a cyclic peptide; a peptide or protein comprising one or more side-chain modified amino acids containing groups composed of fluorine, bromine, iodine, biotin, azide, alkene, alkyne, glycan, lipid, phosphate, polyethylene glycol, thiol, thioester, keto acid, samarium, lanthanum, terbium, and various fluorophores.

36. The method of claim 20, wherein the bioactive moiety comprises an isostere, an N-methyl amide, a circular peptide, an ether peptide, a hydrocarbon linker, a conformation locked peptide, a stapled peptide, a cyclic protein, or a peptidomimetic.

37. The method of claim 20, wherein the bioactive moiety is a D-peptide or a D-protein.

38. The method of claim 20, wherein the bioactive moiety is not a deoxyribonucleic acid (DNA), a ribonucleic acid (RNA), a peptide nucleic acid (PNA), or a natural peptide or protein containing only L-amino acids.

39. A method for delivering a bioactive moiety comprising at least one non-natural component into a cell cytosol of an eukaryotic cell comprising contacting the cell with (a) a fusion molecule comprising the bioactive moiety attached to an A component of a bacterial toxin, a functional wild-type or modified fragment thereof, or an A component surrogate or mimetic; and (b) a corresponding B component of the bacterial toxin or a functional fragment thereof, wherein the bioactive moiety does not comprise a deoxyribonucleic acid (DNA), a ribonucleic acid (RNA), a peptide nucleic acid (PNA), or a natural peptide or protein containing only L-amino acids.

* * * * *

SEQUENCE LISTING

```
<160> NUMBER OF SEQ ID NOS: 19

<210> SEQ ID NO 1
<211> LENGTH: 4
<212> TYPE: PRT
<213> ORGANISM: Unknown
<220> FEATURE:
<223> OTHER INFORMATION: Description of Unknown:
      Caspase-8 protease cleavage peptide

<400> SEQUENCE: 1

Leu Glu Thr Asp
1


<210> SEQ ID NO 2
<211> LENGTH: 8
<212> TYPE: PRT
<213> ORGANISM: Unknown
<220> FEATURE:
<223> OTHER INFORMATION: Description of Unknown:
      Calpain protease cleavage peptide

<400> SEQUENCE: 2

Glu Pro Leu Phe Ala Glu Arg Lys
1               5


<210> SEQ ID NO 3
<211> LENGTH: 6
<212> TYPE: PRT
<213> ORGANISM: Unknown
<220> FEATURE:
<223> OTHER INFORMATION: Description of Unknown:
      Calthepsin L protease cleavage peptide

<400> SEQUENCE: 3

Leu Trp Met Arg Phe Ala
1               5


<210> SEQ ID NO 4
<211> LENGTH: 535
<212> TYPE: PRT
<213> ORGANISM: Corynebacterium diphtheriae

<400> SEQUENCE: 4

Gly Ala Asp Asp Val Val Asp Ser Ser Lys Ser Phe Val Met Glu Asn
1               5                   10                  15
```

-continued

```
Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430
```

-continued

```
Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535


<210> SEQ ID NO 5
<211> LENGTH: 293
<212> TYPE: PRT
<213> ORGANISM: Escherichia coli

<400> SEQUENCE: 5

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270
```

Asn Lys Ile Leu Trp Asp Ser Ser Thr Leu Gly Ala Ile Leu Met Arg
275 280 285

Arg Thr Ile Ser Ser
290

<210> SEQ ID NO 6
<211> LENGTH: 69
<212> TYPE: PRT
<213> ORGANISM: Escherichia coli

<400> SEQUENCE: 6

Thr Pro Asp Cys Val Thr Gly Lys Val Glu Tyr Thr Lys Tyr Asn Asp
1 5 10 15

Asp Asp Thr Phe Thr Val Lys Val Gly Asp Lys Glu Leu Phe Thr Asn
20 25 30

Arg Trp Asn Leu Gln Ser Leu Leu Leu Ser Ala Gln Ile Thr Gly Met
35 40 45

Thr Val Thr Ile Lys Thr Asn Ala Cys His Asn Gly Gly Gly Phe Ser
50 55 60

Glu Val Ile Phe Arg
65

<210> SEQ ID NO 7
<211> LENGTH: 613
<212> TYPE: PRT
<213> ORGANISM: Pseudomonas aeruginosa

<400> SEQUENCE: 7

Ala Glu Glu Ala Phe Asp Leu Trp Asn Glu Cys Ala Lys Ala Cys Val
1 5 10 15

Leu Asp Leu Lys Asp Gly Val Arg Ser Ser Arg Met Ser Val Asp Pro
20 25 30

Ala Ile Ala Asp Thr Asn Gly Gln Gly Val Leu His Tyr Ser Met Val
35 40 45

Leu Glu Gly Gly Asn Asp Ala Leu Lys Leu Ala Ile Asp Asn Ala Leu
50 55 60

Ser Ile Thr Ser Asp Gly Leu Thr Ile Arg Leu Glu Gly Gly Val Glu
65 70 75 80

Pro Asn Lys Pro Val Arg Tyr Ser Tyr Thr Arg Gln Ala Arg Gly Ser
85 90 95

Trp Ser Leu Asn Trp Leu Val Pro Ile Gly His Glu Lys Pro Ser Asn
100 105 110

Ile Lys Val Phe Ile His Glu Leu Asn Ala Gly Asn Gln Leu Ser His
115 120 125

Met Ser Pro Ile Tyr Thr Ile Glu Met Gly Asp Glu Leu Leu Ala Lys
130 135 140

Leu Ala Arg Asp Ala Thr Phe Phe Val Arg Ala His Glu Ser Asn Glu
145 150 155 160

Met Gln Pro Thr Leu Ala Ile Ser His Ala Gly Val Ser Val Val Met
165 170 175

Ala Gln Ala Gln Pro Arg Arg Glu Lys Arg Trp Ser Glu Trp Ala Ser
180 185 190

Gly Lys Val Leu Cys Leu Leu Asp Pro Leu Asp Gly Val Tyr Asn Tyr
195 200 205

Leu Ala Gln Gln Arg Cys Asn Leu Asp Asp Thr Trp Glu Gly Lys Ile
210 215 220

-continued

Tyr Arg Val Leu Ala Gly Asn Pro Ala Lys His Asp Leu Asp Ile Lys
225 230 235 240

Pro Thr Val Ile Ser His Arg Leu His Phe Pro Glu Gly Gly Ser Leu
245 250 255

Ala Ala Leu Thr Ala His Gln Ala Cys His Leu Pro Leu Glu Thr Phe
260 265 270

Thr Arg His Arg Gln Pro Arg Gly Trp Glu Gln Leu Glu Gln Cys Gly
275 280 285

Tyr Pro Val Gln Arg Leu Val Ala Leu Tyr Leu Ala Ala Arg Leu Ser
290 295 300

Trp Asn Gln Val Asp Gln Val Ile Arg Asn Ala Leu Ala Ser Pro Gly
305 310 315 320

Ser Gly Gly Asp Leu Gly Glu Ala Ile Arg Glu Gln Pro Glu Gln Ala
325 330 335

Arg Leu Ala Leu Thr Leu Ala Ala Ala Glu Ser Glu Arg Phe Val Arg
340 345 350

Gln Gly Thr Gly Asn Asp Glu Ala Gly Ala Ala Asn Ala Asp Val Val
355 360 365

Ser Leu Thr Cys Pro Val Ala Ala Gly Glu Cys Ala Gly Pro Ala Asp
370 375 380

Ser Gly Asp Ala Leu Leu Glu Arg Asn Tyr Pro Thr Gly Ala Glu Phe
385 390 395 400

Leu Gly Asp Gly Gly Asp Val Ser Phe Ser Thr Arg Gly Thr Gln Asn
405 410 415

Trp Thr Val Glu Arg Leu Leu Gln Ala His Arg Gln Leu Glu Glu Arg
420 425 430

Gly Tyr Val Phe Val Gly Tyr His Gly Thr Phe Leu Glu Ala Ala Gln
435 440 445

Ser Ile Val Phe Gly Gly Val Arg Ala Arg Ser Gln Asp Leu Asp Ala
450 455 460

Ile Trp Arg Gly Phe Tyr Ile Ala Gly Asp Pro Ala Leu Ala Tyr Gly
465 470 475 480

Tyr Ala Gln Asp Gln Glu Pro Asp Ala Arg Gly Arg Ile Arg Asn Gly
485 490 495

Ala Leu Leu Arg Val Tyr Val Pro Arg Ser Ser Leu Pro Gly Phe Tyr
500 505 510

Arg Thr Ser Leu Thr Leu Ala Ala Pro Glu Ala Ala Gly Glu Val Glu
515 520 525

Arg Leu Ile Gly His Pro Leu Pro Leu Arg Leu Asp Ala Ile Thr Gly
530 535 540

Pro Glu Glu Glu Gly Gly Arg Leu Glu Thr Ile Leu Gly Trp Pro Leu
545 550 555 560

Ala Glu Arg Thr Val Val Ile Pro Ser Ala Ile Pro Thr Asp Pro Arg
565 570 575

Asn Val Gly Gly Asp Leu Asp Pro Ser Ser Ile Pro Asp Lys Glu Gln
580 585 590

Ala Ile Ser Ala Leu Pro Asp Tyr Ala Ser Gln Pro Gly Lys Pro Pro
595 600 605

Arg Glu Asp Leu Lys
610

<210> SEQ ID NO 8
<211> LENGTH: 194

<212> TYPE: PRT
<213> ORGANISM: Vibrio cholerae

<400> SEQUENCE: 8

```
Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
65                  70                  75                  80

Ser Thr Tyr Tyr Leu Tyr Val Leu Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser Ser
```

<210> SEQ ID NO 9
<211> LENGTH: 46
<212> TYPE: PRT
<213> ORGANISM: Vibrio cholerae

<400> SEQUENCE: 9

```
Met Ser Asn Thr Cys Asp Glu Lys Thr Gln Ser Leu Gly Val Lys Phe
1               5                   10                  15

Leu Asp Glu Tyr Gln Ser Lys Val Lys Arg Gln Ile Phe Ser Gly Tyr
            20                  25                  30

Gln Ser Asp Ile Asp Thr His Asn Arg Ile Lys Asp Glu Leu
        35                  40                  45
```

<210> SEQ ID NO 10
<211> LENGTH: 103
<212> TYPE: PRT
<213> ORGANISM: Vibrio cholerae

<400> SEQUENCE: 10

```
Thr Pro Gln Asn Ile Thr Asp Leu Cys Ala Glu Tyr His Asn Thr Gln
1               5                   10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Ser Ser Gln His Ile Asp Ser Gln Lys Lys Ala
    50                  55                  60
```

Ile Glu Arg Met Lys Asp Thr Leu Arg Ile Ala Tyr Leu Thr Glu Ala
65 70 75 80

Lys Val Glu Lys Leu Cys Thr Trp Asn Asn Lys Thr Pro His Ala Ile
85 90 95

Ala Ala Ile Ser Met Ala Asn
100

<210> SEQ ID NO 11
<211> LENGTH: 12
<212> TYPE: PRT
<213> ORGANISM: Bacillus anthracis

<400> SEQUENCE: 11

Ala Gly Gly His Gly Asp Val Gly Met His Val Lys
1 5 10

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 12

His His His His His His
1 5

<210> SEQ ID NO 13
<211> LENGTH: 28
<212> TYPE: PRT
<213> ORGANISM: Bacillus anthracis

<400> SEQUENCE: 13

Ala Gly Gly His Gly Asp Val Gly Met His Val Lys Glu Lys Glu Lys
1 5 10 15

Asn Lys Asp Glu Asn Lys Arg Lys Asp Glu Glu Arg
20 25

<210> SEQ ID NO 14
<211> LENGTH: 17
<212> TYPE: PRT
<213> ORGANISM: Bacillus anthracis

<400> SEQUENCE: 14

Lys Glu Lys Glu Lys Asn Lys Asp Glu Asn Lys Arg Lys Asp Glu Glu
1 5 10 15

Arg

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Lys Glu Lys Glu Lys Glu Lys Glu Lys Glu Lys Glu Lys Glu Lys Glu
1 5 10 15

Lys

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (16)..(16)
<223> OTHER INFORMATION: Cysteic acid

<400> SEQUENCE: 16

```
Lys Glu Lys Glu Lys Asn Lys Asp Glu Asn Lys Arg Lys Asp Glu Cys
1               5                   10                  15

Arg
```

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(16)
<223> OTHER INFORMATION: Cysteic acid

<400> SEQUENCE: 17

```
Lys Glu Lys Glu Lys Asn Lys Asp Glu Asn Lys Arg Lys Cys Cys Cys
1               5                   10                  15

Arg
```

<210> SEQ ID NO 18
<211> LENGTH: 5
<212> TYPE: PRT
<213> ORGANISM: Unknown
<220> FEATURE:
<223> OTHER INFORMATION: Description of Unknown: Sortase A peptide motif

<400> SEQUENCE: 18

```
Leu Pro Ser Thr Gly
1               5
```

<210> SEQ ID NO 19
<211> LENGTH: 263
<212> TYPE: PRT
<213> ORGANISM: Bacillus anthracis

<400> SEQUENCE: 19

```
Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Val Pro Arg Cys Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95
```

-continued

```
Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg
            260
```